United States Patent [19]

Parker et al.

[11] Patent Number: 5,653,742

[45] Date of Patent: Aug. 5, 1997

[54] USE OF BIORESORBABLE POLYMERS IN COCHLEAR IMPLANTS AND OTHER IMPLANTABLE DEVICES

[75] Inventors: John L. Parker, Lane Cove; Claudiu G. Treaba, Wollstonecraft, both of Australia

[73] Assignee: Cochlear Pty. Ltd., Lane Cove, Australia

[21] Appl. No.: 550,912

[22] Filed: Oct. 31, 1995

[30] Foreign Application Priority Data

Sep. 20, 1995 [WO] WIPO .................. PCT/AU95/00622

[51] Int. Cl.$^6$ .................................................. A61N 1/05
[52] U.S. Cl. .............................................. 607/137; 607/116
[58] Field of Search .................................. 607/115, 116, 607/136, 137, 55–57; 600/25; 604/105, 106, 265

[56] References Cited

U.S. PATENT DOCUMENTS

| 3,736,939 | 6/1973 | Taylor | 604/265 |
|---|---|---|---|
| 3,815,608 | 6/1974 | Spinosa et al. | 604/105 |
| 4,257,421 | 3/1981 | Beal | 604/265 |
| 4,284,085 | 8/1981 | Hansen et al. | 128/784 |
| 4,687,480 | 8/1987 | Laby et al. | 604/105 |
| 4,827,940 | 5/1989 | Mayer et al. | 128/642 |
| 5,256,146 | 10/1993 | Ensminger et al. | 604/106 |
| 5,522,876 | 6/1996 | Rusink | 607/127 |

Primary Examiner—William E. Kamm
Assistant Examiner—George Evanisko
Attorney, Agent, or Firm—Gottlieb, Rackman & Reisman

[57] ABSTRACT

An implant such as a cochlear assembly, or other similar device, includes an elongated therapeutic member arranged and constructed to perform a therapeutic function. The therapeutic member has at least two configurations: an insertion and a deployed configuration. The first configuration is selected to ease the insertion of the member into a body cavity. A stiffening member is used to urge said therapeutic member toward said first configuration. The stiffening member is made of a bioresorbable material so that after insertion, the stiffening member dissolves and allows the therapeutic member to assume the second configuration.

13 Claims, 5 Drawing Sheets

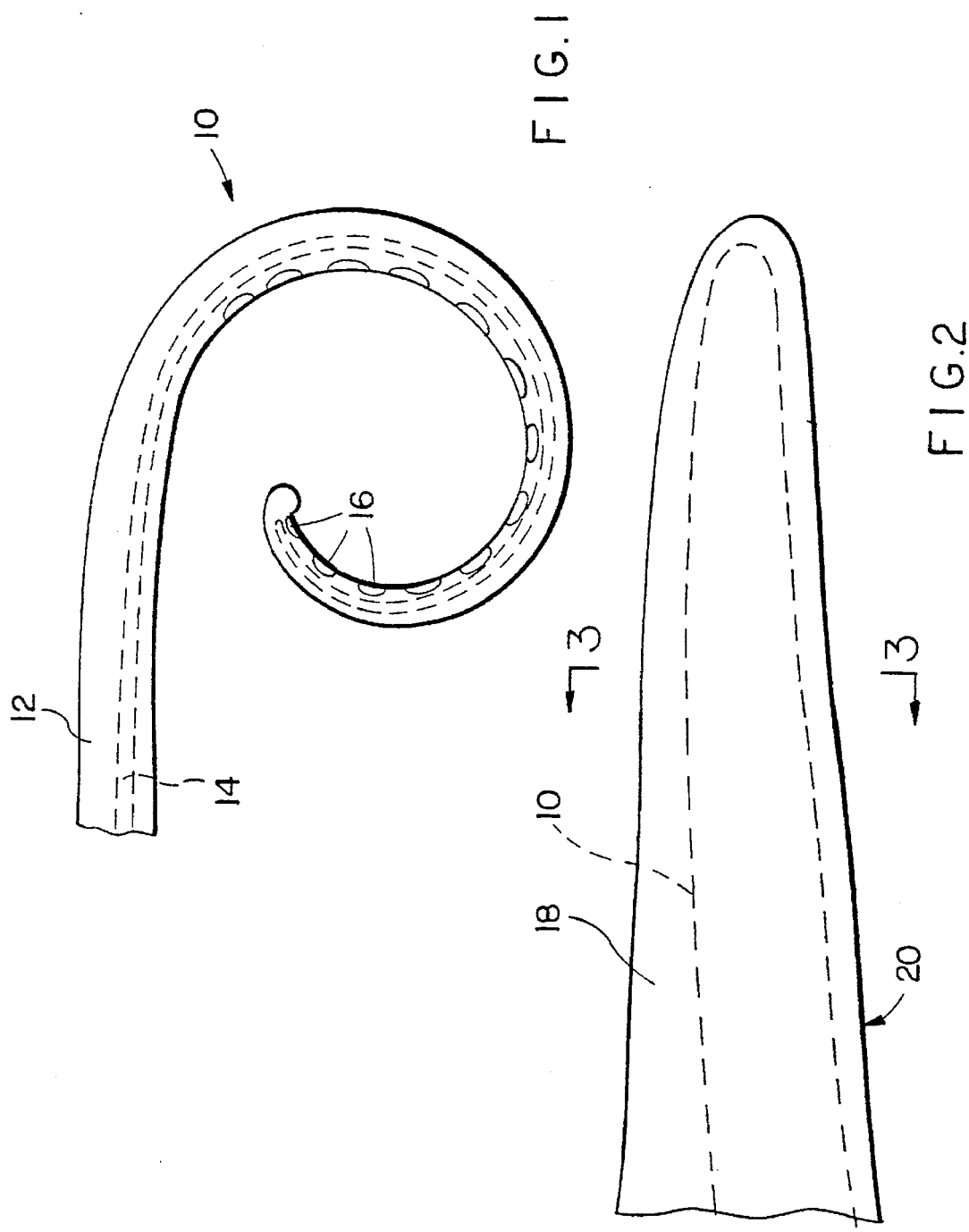

USE OF BIORESORBABLE POLYMERS IN COCHLEAR IMPLANTS AND OTHER IMPLANTABLE DEVICES

BACKGROUND OF THE INVENTION

A. Field of Invention

This invention pertains to implantable devices such as cochlear electrodes incorporating bioresorbable materials, and more particularly to a device which has a first preselected shape suitable for insertion into the body of a patient, and a second shape suitable for providing a specific function, or stimulus, the bioresorbable materials being used to change the device from the second to the first shape.

B. Background of the Invention

The invention is described for electrodes used in cochlear implant systems, however, it is equally applicable to other implantable devices. Cochlear implant systems are used to aid patients having a hearing deficiency. More particularly, these systems include a microphone receiving ambient sounds and converting the sounds into corresponding electrical signals, signal processing means of processing the electrical signals and generating cochlea stimulating signals and an electrode assembly for applying the cochlea stimulating signals to the cochlea of the patient. It is known in the art that the cochlea is tonotopically mapped. In other words, the cochlea can be partitioned into regions, with each region being responsive to signals in a particular frequency range. This property of the cochlea is exploited by providing the electrode assembly with an array of electrodes, each electrode being arranged and constructed to deliver a cochlea stimulating signal within a preselected frequency range to the appropriate cochlea region. The electrical currents and electric fields from each electrode stimulate the cilia disposed on the modiola of the cochlea. Several electrodes may be active simultaneously.

It has been found that in order for these electrodes to be effective, the magnitude of the currents flowing from these electrodes and the intensity of the corresponding electric fields, are a function of the distance between the electrodes and the modiola. If this distance is great, the threshold current magnitude must be larger than if the distance is smaller. Moreover, the current from each electrode may flow in all directions, and the electrical fields corresponding to adjacent electrodes may overlap thereby causing cross-electrode interference. In order to reduce the threshold stimulation amplitude and to eliminate cross electrode interference, it is advisable to keep the distance between the electrode array and the modiola as small as possible. This is best accomplished by providing the electrode array in the shape which generally follows the shape of the modiola. Of course during insertion, the electrode assembly should be generally straight, because otherwise the insertion procedure is too cumbersome and difficult.

Several methods and means of curving the electrode assembly, however in the opinion of the inventors, none of these prior methods are satisfactory. For example, one electrode assembly is known which includes an electrode carrier provided with a longitudinal element arranged on one side of the carrier and constructed to change its dimension once the assembly is inserted. For example, the longitudinal element could include a hydrogel such as PAA (Polyacrylic acid) which expands after insertion by absorbing water from the cochlear fluid. Alternatively, the longitudinal element could be a bimetallic filament (such as nickel/titanium) which is shaped to allow the electrode carrier to take a straight configuration at room temperature but bends into a preselected shape once it is exposed to body temperature.

Another proposed electrode assembly included a mechanical member arranged to bend the electrode carrier after the carrier has been inserted.

All these prior art devices require a structure which is difficult and expensive to manufacture and which in most cases are not expected to perform satisfactorily.

OBJECTIVES AND SUMMARY OF THE INVENTION

In view of the above-mentioned disadvantages of the prior art, it is an objective of the present invention to provide a cochlear electrode assembly which has a first, relatively straight configuration so that it can be readily implanted, and a second, curved configuration to conform to the cochlea of a patient, using a material which dissolves in body fluids.

A further objective is to provide an assembly which has relatively few parts so that its cross-section is not too large for implantation.

Another objective is to provide an assembly which can be manufactured relatively easily and inexpensively.

Other objectives and advantages of the invention shall become apparent from the following description. Briefly, an electrode assembly constructed in accordance with this invention includes an electrode carrier constructed and arranged to support a plurality of electrodes suitable for defining an electrode array for application for cochlear stimulation signals. The carrier is preferably preshaped into a curved configuration selected to insure that the electrodes are disposed in close proximity to the modiola of the scala tympani. Prior to implanting, the carrier is imbedded in a relatively straight sheath or alternatively a stiffening elements is applied to maintain the carrier in a linear configuration. The sheath or the stiffening element is made of a bioresorbable material, such as a polymer which dissolves in the cochlear fluid after implantation. Preferably the carrier is provided with biasing fins which in the linear configuration are folded against the carrier. Once the sheath is dissolved, the biasing fins flex outwardly away from the carrier to engage the walls of the scala tympani to urge the carrier toward the modiola. Alternatively, the carrier is pre-formed so that after the sheath dissolves, the carrier assumes the curved shape.

BRIEF DESCRIPTION OF THE DRAWINGS

FIG. 1 shows a side view of an electrode carrier constructed in accordance with this invention;

FIG. 2 shows an electrode assembly constructed in accordance with this invention with the carrier of FIG. 1 embedded in a stiffening sheath;

DETAILED DESCRIPTION OF THE INVENTION

Figure 3:
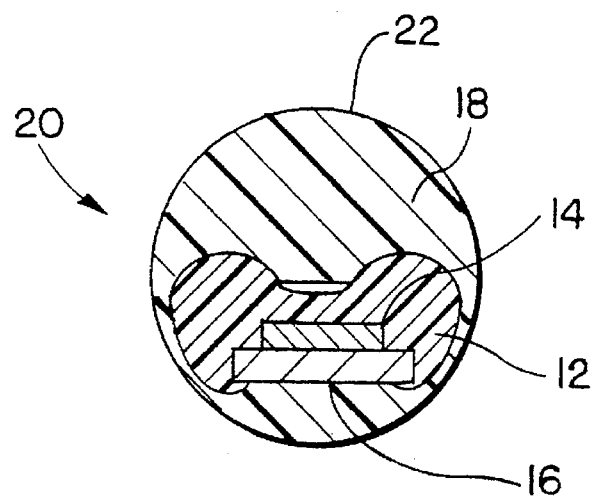
FIG. 3 shows a cross-sectional view of the assembly of FIG. 2 taken along line 3—3.

Referring now to FIG. 1, an electrode assembly constructed in accordance with this invention includes an electrode carrier 10 formed of an elongated member 12 made of a plastic material such as Silastic MDX 4-4210. Imbedded in this member 12 is a cable 14 formed of several insulated wires (not shown), each wire terminating in an electrode 16. The cable 14 is connected to a cochlear stimulation device (not shown) and is used to transmit stimulation pulses from the device to the electrodes 16. As seen in FIG. 1, the electrodes 16 are all exposed. The member 12 is elastic, however, it is made from a material which has shape memory and is pre-curved so that its natural configuration is in the shape of a spiral as shown. The curvature of the spiral follows the curvature of the scala tympani of the person, and more particularly, the curvature of the modiola, as shall be described in more detail below.

After its completion, carrier 10 is distorted so that its configuration is substantially straight and is embedded into a sheath 18, as shown in FIG. 2, thus forming an electrode assembly 20. Sheath 18 is made of a relatively stiff material so that it is able to retain the carrier 10 in the straight configuration shown. Importantly, sheath 18 is made of a material which dissolves, is bioresorbable or is otherwise biodegradable when immersed in cochlear fluid. For example, sheath 18 may be made of polyvinyl alcohol (PVA), polylactic acid (PLA), polyglycolic acid (PGA) and other similar compounds. Preferably the sheath 18 is made with a smooth outer surface to allow the assembly 20 to be implanted easily. A coating may be applied to this surface to reduce friction. The coating may be made of a time-released antimicrobial material to provide protection against infections during implantation. Sheath 18, while stiffer than carrier 10, must be sufficiently flexible so that it can be bent to conform to the shape of the cochlea.

A cross section for the assembly 20 is shown in FIG. 3. As can be seen in this Figure, the member 12 is preferably flattened, or in the shape of a figure 8 so that it can bend more easily in a plane normal to the electrode 16.

Figure 4:
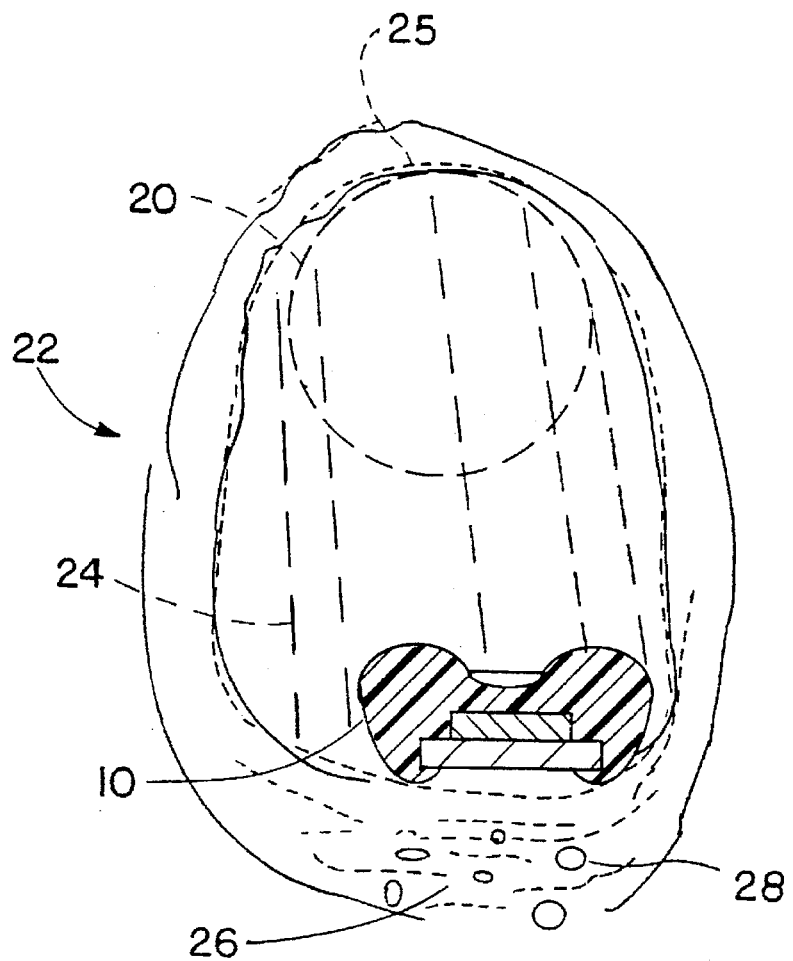
FIG. 4 shows a cross sectional view of the scala tympani of a patient with the electrode carrier of FIG. 1 after the sheath has been dissolved.

The initial position of electrode assembly immediately after implantation, and the carrier 10 after the sheath 18 is dissolved can be seen in FIG. 4. In this Figure, assembly 20 has been implanted into the scala tympani 22 so that it is immersed in the cochlear fluid 24. Initially, because of the stiffness of sheath 18, the assembly maintains a large radius of curvature so that it is disposed adjacent wall 25 of scala tympani 22. However in a relatively short time that can be controlled and is to be determined by the intended insertion procedures the sheath 18 dissolves in the cochlear fluid 24 releasing the carrier 10. As a result the carrier resumes its natural spiral configuration shown in FIG. 1. In this configuration, the carrier 10 is disposed adjacent to the modiola 26. Importantly, in this latter configuration, the electrodes 16 are facing the modiola 26 so that they are positioned as close as possible to the spiral ganglia 28 thereof. In this manner, the electrodes 16 can generate currents and electric fields with a relatively small intensity without causing cross-channel interference.

Figure 5:
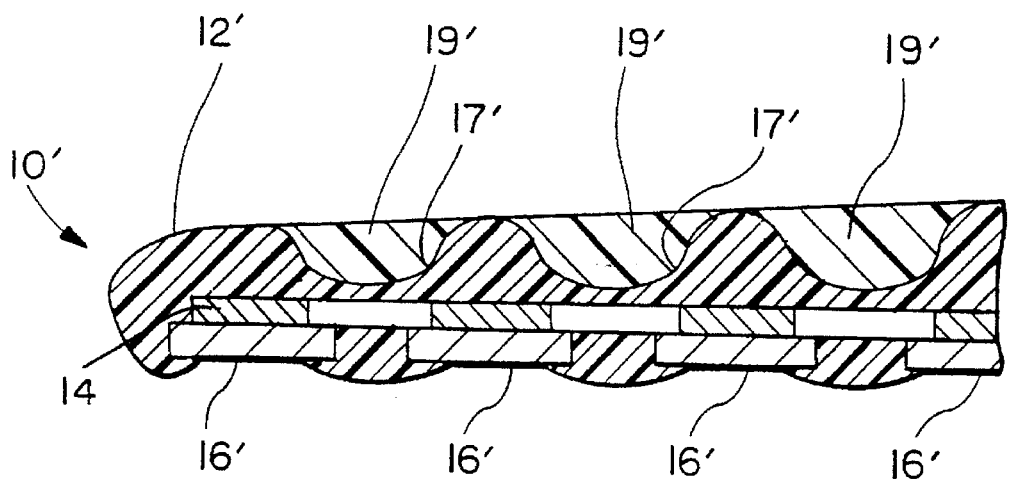
FIG. 5 shows a longitudinal cross-sectional view of an electrode carrier in accordance with a first alternate embodiment.

In the embodiment of FIG. 5, the carrier 10' is formed of a longitudinal support member 12' with connecting wires 14' and electrodes 16'. The carrier 10' is preformed into spiral shape similar to the shape of carrier 10 on FIG. 1. Importantly the member 12' is formed on a side opposite electrodes 16' with a plurality of depressions or dimples 17'. The purpose of these dimples is to hold a stiffener material 19'. The stiffener 19' material is introduced into the dimples only after the carrier 10' is deformed to assume a straight or linear configuration, as seen in FIG. 5. The material is the same material as the material of sheath 18, that is, it is bioresorbable. In the embodiment of FIG. 5, the material 19' provides rigidity to the carrier 10' to prevent the carrier 10' from taking its spiral shape. In this manner, the carrier 10' can be readily implanted into the scala tympani. After implantation, the material 19' dissolves in the cochlear fluid and allows the carrier 10' to move back to its spiral shape.

Figure 9:
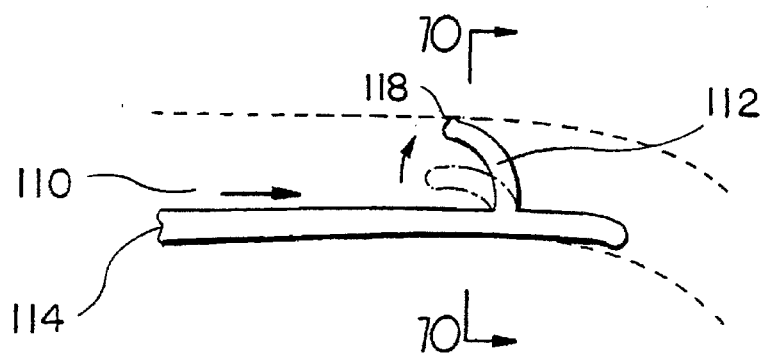
FIG. 9 shows the carrier of FIG. 7 deployed in the scala tympani, after dissolution of the stiffening sheath.
Figure 6:
FIG. 6 shows a side view of an electrode carrier in accordance with a second alternate embodiment of the invention.
Figure 8:
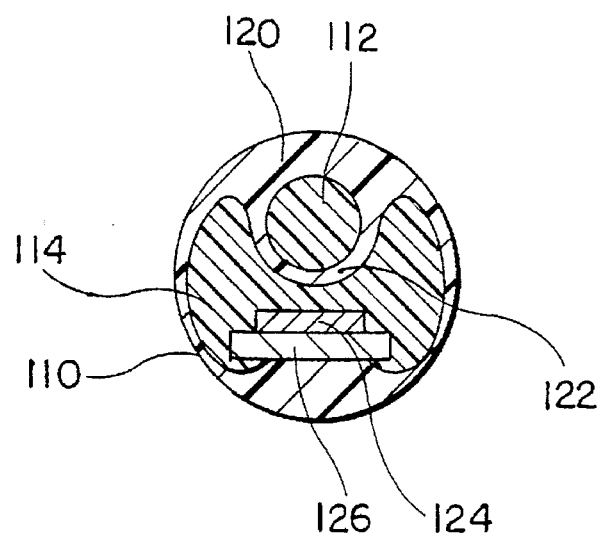
FIG. 8 shows a cross sectional view of the assembly of FIG. 7 taken along line 8—8.
Figure 10:
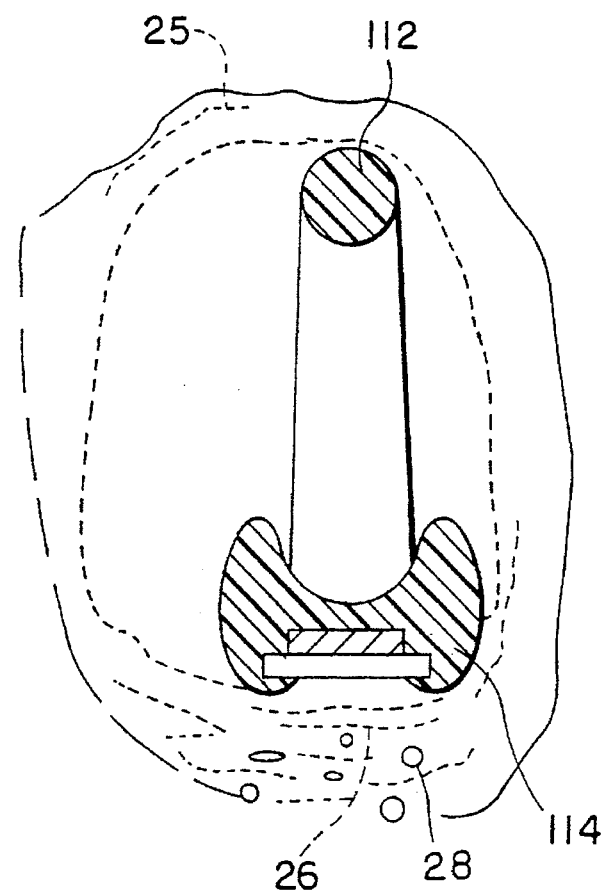
FIG. 10 shows a cross-sectional view of the carrier of FIG. 9 taken along line 10—10.
Figure 11:
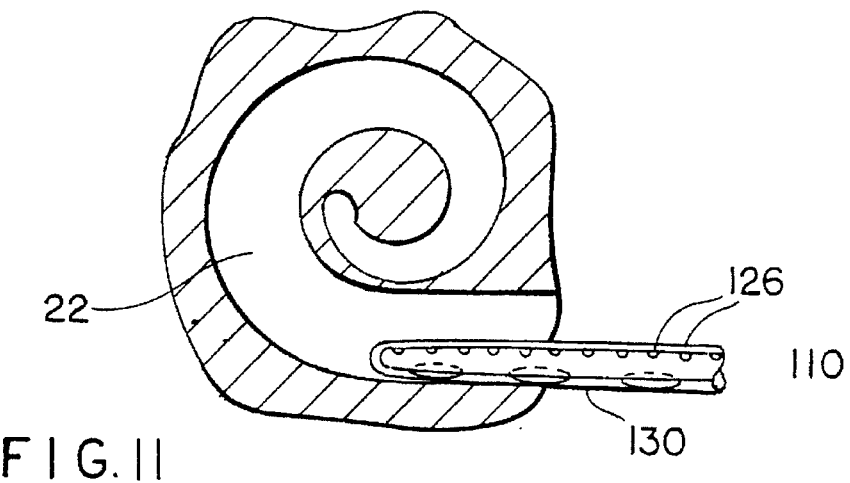
FIG. 11 shows a somewhat diagrammatic view of the assembly of FIG. 7 being inserted in to the scala tympani.
Figure 12:
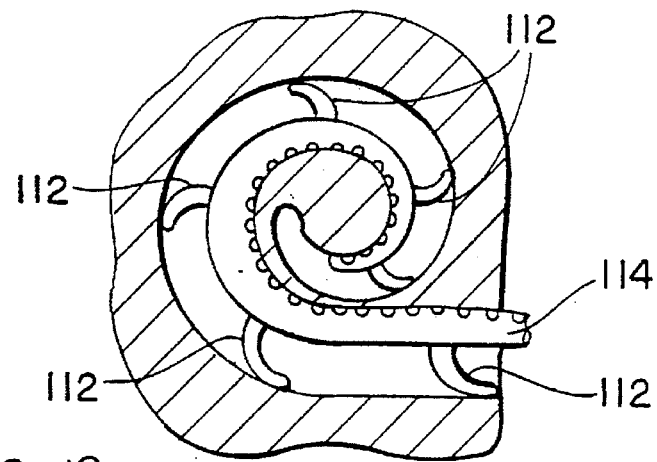
FIG. 12 shows a somewhat diagrammatic view of the carrier of FIG. 11 deployed in the scala tympani.
Figure 13:
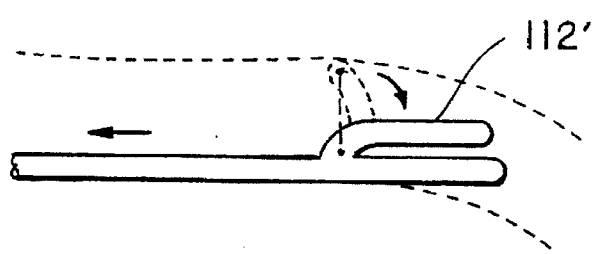
FIG. 13 shows the electrode carrier of FIG. 11 being withdrawn from the scala tympani.
Figure 7:
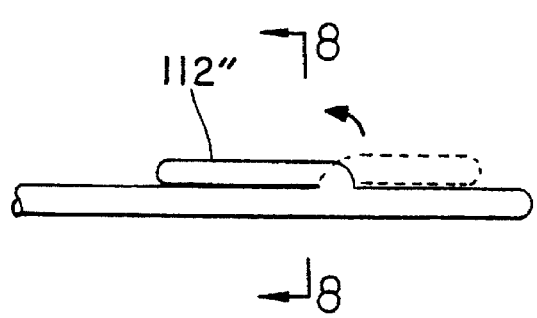
FIG. 7 shows the carrier of FIG. 6 embedded in a stiffening sheath.

Yet another embodiment of the invention is shown in FIG. 6. In this embodiment, carrier 110 is provided with a plurality of longitudinally spaced fins 112 formed on generally tubular body 114. The fins 112 are relatively elastic. In the normal position as shown in. FIG. 6, these fins 112 extend towards the tip of the carrier. Preferably the free ends 118 of the fins are curved slightly in the longitudinal direction. After the carrier 110 is formed as shown in FIG. 6, the fins are forced into a position where they are disposed generally in parallel with and adjacent to the body 114 as shown somewhat diagrammatically in FIG. 7. The carrier 110 thus deformed is then encased in a sheath 120 formed of a biodegradable material like sheath 18. In order to reduce the cross sectional dimensions of the carrier in this second configuration, the body 114 may be formed with a channel. Thus for example, the carrier 110 may include body 114 formed with a channel 122 for housing, in the second configuration, fin 112. As with the previous embodiment, the carrier 110 also includes connecting wires 124 imbedded in body 114 and a plurality of electrodes 126. The advantage of this embodiment is that, after the assembly of FIG. 8 is implanted, and after the sheath 120 dissolves, the fins 112 are released from channel 122 until their free ends 118 engages wall 25, thereby urging and biasing body 114 toward the modiola 26, as shown in FIGS. 9 and 10. This whole process is shown in more detail in FIGS. 11 and 12. The assembly 130 formed of the carrier 110 and sheath 120, as shown in FIG. 8, is first inserted into the scala tympani 22. After the assembly 130 is fully inserted, the sheath 120 dissolves leaving the carrier 110 firmly seated with the scala tympany 22 as seen in FIG. 12. If it is required to remove the carrier 110 for any reason, as indicated in FIG. 13 in the direction A, the fins 112 bend back to the position 112', as shown.

As can be seen in FIG. 12, the carrier 110 is firmly seated and positioned in the scala tympani by the interference fit and biasing provided by the fins 112 between the body 114 and the walls of the scala tympani 22. Therefore, the body 114 can, but need not be, made in the spiral shape shown in FIG. 1, and need not be made of a shape-retaining material, like carrier 10.

Although the preferred embodiments of the invention have been described in conjunction with a cochlear electrode assembly, it should be understood that its teachings may be applicable for other implanted electrode, such as the electrodes used in pacemakers. For this latter implementation of the invention, the tines used to secure the distal end of the electrode to an internal cardiac wall, are initially folded and maintained in a closed positioned by a bioabsorbable sheath or other similar means in a manner similar to the way the fins 112 are folded in FIG. 7. After implantation the sheath dissolves allowing the tines to open and engage the cardiac walls, thereby securing the electrode.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

We claim:

1. An implantable therapeutic device comprising:

an elongated member having a plurality of electrodes mounted on said member and having a first configuration selected to allow said member to be inserted into a patient's body and a second configuration wherein said elongated member is adapted to apply a preselected therapy with said electrodes, said elongated member being made of a first material, said first material being flexible; and a sheath enveloping said elongated member, said sheath having a shape selected for biasing said elongated member into said first configuration, said sheath being made of a second material stiffer than said first material, wherein said second material is soluble in body fluids, so that after insertion into said body, said sheath dissolves, allowing said sheath to take said second configuration.

2. The device of claim 1 wherein said elongated member is preformed to said second configuration.

3. The device of claim 1 wherein said elongated member includes a longitudinal body made of an elastic material and a plurality of fins attached to said body, said fins being constructed and arranged for positioning said elongated member to said second configuration after said stiffening member has dissolved.

4. The device of claim 3 wherein said fins are disposed adjacent to said body in said first configuration.

5. A cochlear implant electrode assembly comprising:

an elongated electrode carrier having an elastic body, said body having a first configuration for insertion into a patient's cochlea, and a second configuration in which said carrier is curved to match a surface of said cochlea;

a plurality of electrodes mounted on said carrier; and stiffening sheath disposed about said carrier for setting said body into said first configuration, said stiffening sheath being stiffer than said elastic body, said stiffening sheath being made of a bioresorbable material which dissolves on insertion into said cochlea to permit said body to take said second configuration.

6. The assembly of claim 5 wherein in said first configuration said body is substantially straight.

7. The assembly of claim 5 wherein said body is provided with a plurality of elastic fins which in said first configuration are disposed adjacent to said body, and in said second configuration extend away from said body to engage a cochlear wall.

8. The assembly of claim 7 wherein said body is formed with a channel, and in said first configuration said fins are disposed in said channel.

9. The assembly of claim 5 wherein said body is made of a plastic material with memory and is preformed to said first configuration.

10. The assembly of claim 9 wherein said body is made with a plurality of indentations and said stiffening means includes a stiffening material disposed in said indentations.

11. The device of claim 5 wherein said bioresorbable material is selected from the group consisting of polyvinyl alcohol, polylactic acid and polyglycolic acid.

12. A method of making a therapeutic device, said device having a body with a plurality of electrodes on said body and with a first configuration selected for ease of insertion and a second configuration for application of therapy with said electrodes, said method comprising the steps of:

forming said body;

setting said body into said first configuration; and applying a sheath about said body, said sheath being made of a bioresorbable material, whereby when said assembly is inserted into a patient, said sheath dissolves allowing said body to take said second configuration.

13. The method of claim 12 wherein said body is first preformed to said second configuration.

* * * * *

UNITED STATES PATENT AND TRADEMARK OFFICE
CERTIFICATE OF CORRECTION

PATENT NO. : 5,653,742

DATED : August 5, 1997

INVENTOR(S) : John L. Parker, Claudiu G. Treaba

It is certified that error appears in the above-identified patent and that said Letters Patent is hereby corrected as shown below:

Column 3

Claim 1, line 16, change "sheath" to -- elongated member --.

Claim 3, lines 5-6, change "stiffening member" to -- sheath --.

Claim 5, line 7, prior to "stiffening" insert -- a --.

Claim 10, line 2, insert --sheath-- after "stiffening", and delete --means--.

Signed and Sealed this

Twentieth Day of January, 1998

Attest:

BRUCE LEHMAN

Attesting Officer

Commissioner of Patents and Trademarks